US008409871B2

(12) United States Patent
Drummond

(10) Patent No.: US 8,409,871 B2
(45) Date of Patent: Apr. 2, 2013

(54) METHOD OF TREATMENT OF TISSUE PROCESSING FLUID AND APPARATUS THEREFOR

(75) Inventor: Michael Houston Drummond, Glen Waverley (AU)

(73) Assignee: Leica Biosystems Melbourne Pty Ltd, Victoria (AU)

( * ) Notice: Subject to any disclaimer, the term of this patent is extended or adjusted under 35 U.S.C. 154(b) by 1236 days.

(21) Appl. No.: 11/569,658

(22) PCT Filed: May 24, 2005

(86) PCT No.: PCT/AU2005/000737
§ 371 (c)(1),
(2), (4) Date: May 12, 2008

(87) PCT Pub. No.: WO2005/116609
PCT Pub. Date: Dec. 8, 2005

(65) Prior Publication Data
US 2008/0248560 A1   Oct. 9, 2008

(30) Foreign Application Priority Data

May 25, 2004   (AU) ............................... 2004902790

(51) Int. Cl.
*G01N 1/36* (2006.01)
(52) U.S. Cl. ........................................ 436/174; 436/177
(58) Field of Classification Search ................ 436/174, 436/177, 181, 8, 18; 23/293 R, 306, 307; 203/1, 2, 39, 91; 435/40.5, 40.51, 40.52
See application file for complete search history.

(56) References Cited

U.S. PATENT DOCUMENTS

| 3,871,574 | A | 3/1975 | Lucas |
| 4,099,483 | A | 7/1978 | Henderson |
| 6,042,874 | A | 3/2000 | Visinoni et al. |
| 6,207,408 | B1 | 3/2001 | Essenfeld et al. |
| 2002/0029953 | A1 | 3/2002 | Cole |
| 2002/0131896 | A1 | 9/2002 | Hunnell et al. |

FOREIGN PATENT DOCUMENTS

| DE | 198 41 556 C1 | | 3/2000 |
| GB | 2065912 A | * | 7/1981 |
| WO | 03/29845 A2 | | 4/2003 |
| WO | 2005/031312 A1 | | 4/2005 |

* cited by examiner

*Primary Examiner* — Yelena G Gakh
*Assistant Examiner* — Christopher A Hixson
(74) *Attorney, Agent, or Firm* — Sughrue Mion, PLLC

(57) ABSTRACT

The present invention relates to the field of tissue processing, particularly, to the treatment of fluids used in tissue processing. In one embodiment the present invention provides for treating a tissue processing fluid comprising first processing fluid comprising a first processing fluid and a second contaminating fluid, by: gradually varying the pressure of the fluid from an initial pressure level to a first pressure level such that the fluid remains below a vaporizing point of the second contaminating fluid and, heating the fluid to at least a vaporizing temperature of the second contaminating fluid. In another embodiment, the present invention removes the second contaminating fluid from the fluid by varying at least one of the pressure and temperature of the fluid so as to allow the second contaminating fluid to vaporize. Alternatively, an embodiment of the present invention interleaves the step of removing with one or more tissue processing protocol steps. In a preferred embodiment, the invention relates to the treatment of infiltrating materials, particularly in their liquid form in a histological tissue sample processor capable of Xylene free operation.

21 Claims, 3 Drawing Sheets

METHOD OF TREATMENT OF TISSUE PROCESSING FLUID AND APPARATUS THEREFOR

RELATED APPLICATIONS

This application claims priority to Australian Provisional Patent Application No. 2004902790, filed 25 May 2004 entitled "Method of Treatment of Tissue Processing Fluid and Apparatus Therefor" and, the specification thereof is incorporated herein by reference in its entirety and for all purposes.

FIELD OF INVENTION

The present invention relates to the field of tissue processing. In particular, the present invention relates to the treatment of fluids used in tissue processing. In one form, the invention relates to the treatment of infiltrating materials, particularly in their liquid form. It will be convenient to hereinafter describe the invention in relation to the use of paraffin wax in a histological tissue sample processor capable of Xylene free operation; however, it should be appreciated that the present invention may not be limited to that use, only.

RELATED ART

The inventor has identified the following related art. Histological tissue specimen preparation is a physical process that involves chemical solutions reacting with biological specimens. The end result of such treatment is a sample that has had water removed, and been infiltrated with material such as paraffin wax. Once the tissue has been embedded in the paraffin wax, it is stable and may then be sectioned on a rotary microtome. This tissue processing typically involves four different sub-procedures involving a number of reagents and infiltrating material(s), which are referred to hereafter collectively and/or in combination as fluids:

(a) Fixation

Fixation is a process by means of which cell proteins are stabilised, and the process is normally performed using chemical solutions. A good fixative is usually a fluid, which will neither shrink nor swell the tissue, and more particularly will not dissolve its constituent parts, but will kill bacteria and moulds, and render enzymes inactive. In addition, the solution must modify tissue constituents in such a way that they retain their form when subjected to treatment that would have damaged them in their initial state. The most commonly used chemical solution is Formalin.

(b) Dehydration

Since the ultimate purpose of tissue specimen treatment is to embed the tissue sample within an infiltrating material, eg paraffin wax, and since water and paraffin wax are not miscible, the sample must be dehydrated after the fixation step. This is usually achieved by subjecting the tissue sample to increasing concentrations of alcohols.

(c) Clearing

After dehydration, the tissue sample may still not be capable of accepting paraffin wax since paraffin wax and alcohol are not miscible. A chemical solution, selected to be miscible with both alcohol and paraffin, may be used to clear the alcohol from the sample. The chemical solution most commonly used is Xylene, although chloroform may also be used. Unfortunately, these solutions may be considered toxic. Xylene, for example, is considered to be toxic although most histological processing laboratories use Xylene on a daily basis.

(d) Infiltration

The fourth and final step in the tissue sample treatment is infiltrating the sample, usually with paraffin wax. In this step the cleared tissue samples are placed into paraffin wax heated to a few degrees above its liquefaction temperature. Several changes of paraffin wax may be required to remove the residual Xylene so that the tissue is completely infiltrated with the molten paraffin wax.

The timing of the fluid change for all the fluids relates to the requirement to effectively displace the previous chemical from the tissue samples. Tissue samples can vary considerably in content and size, and therefore there may be a large variation in the time required to displace the fluid from one sample compared to the time taken to displace fluid from another. Further, some samples are sandwiched between biopsy pads that are porous and absorb significant quantities of fluid.

An attempt at automation of the previously manual method of tissue processing involved placing solutions in a circular arrangement so that samples could be moved from container to container until they reached the last heated paraffin wax reservoir. An example of an instrument with this type of configuration used in the histology field was the Technicon™ instrument. One of the major disadvantages of instruments of this type was that they allowed fumes to escape into the laboratory, thus exposing the laboratory workers to a hazardous environment. To overcome this problem, the next generation of tissue processing instruments included a centrally located closed chamber for the tissue samples. The solutions necessary for tissue processing were delivered into the closed chamber where the fluids are pumped in and out of the chamber in sequence. Normally the chamber would not be opened during the process.

Tissue processing may be broken into sequential steps as mentioned above. The particular fluids used, temperatures and times of exposure may be defined in a protocol.

As the chamber is closed, and only a single protocol can be run, the protocol must attempt to cater for the range of tissue samples that may be included in a single run. This can result in either over processing or under processing of some samples. Given the sealed nature of the retort, tissue samples may not easily be removed or added during a processing run.

Another problem is that some samples require urgent processing, while other samples are not urgent. In the known tissue sample preparation apparatus it has not been possible to stop a current sample run to process a sample required urgently, or to employ a protocol that allows an urgently required sample to be processed with other samples that require longer processing times. Thus, either the urgently required sample is run in isolation, or it is put with other samples, increasing the processing time.

Examples of known automated tissue processing machines will be found in the patent literature, and typical examples include U.S. Pat. No. 4,141,312 Louder, and U.S. Pat. No. 5,049,510 Repasi et al.

The prior art has therefore been unable to deal adequately with ensuring that a variety of samples can be processed safely and efficiently.

Some systems include heating of wax or tissue samples with microwaves, however microwave systems are difficult to automate, and may preferentially heat the tissue sample rather than the reagents. These systems are known to be able to process up to only about 80 tissue cassettes in a run. Lower throughputs are due, in part, to the limitations introduced by the need to supply power to the microwave source.

Many, if not all, of the above problems have been addressed by the Peloris™ Tissue Processor manufactured and sold by, Vision BioSystems Limited, the present Applicant. With further reference to related art tissue processing systems, the following has been identified. When processing tissue, at the first infiltrating step the infiltrating material may become contaminated with the previous processing fluid. This contaminating fluid could be Xylene, some other clearing fluid or, in Xylene free systems, the dehydrating fluid. It is desirable to remove the previous fluid to ensure good tissue processing quality. When the infiltrating material, eg wax, is used repeatedly, it may become more contaminated with previous fluids. As the contaminated infiltrating material is drawn into the processing retort and subjected to standard protocol conditions the contaminants may vaporise. If the vaporising rate is too rapid then the wax may form a foam which sits on top of the wax and this may be drawn into other systems, such as the air system of the tissue processor where it may solidify preventing the instrument from working. In ordinary operation of tissue processors, initially the infiltrating material added to the retort is not boiling at ambient pressure and is at a relatively low temperature of about 60-65° C. Vacuum may then be applied to the infiltrating material, which thereafter may be heated to a moderately higher temperature. With respect to the Peloris™ Tissue Processor, it is possible to firstly heat the infiltrating material to a relatively high temperature of about 85° C. and then have vacuum applied. Lowering the pressure by applying the vacuum lowers the vaporising temperature of the contaminants within the infiltrating material, and this vaporising temperature may be significantly below the operating temperature of the infiltrating material. In fact, in related art systems, the vaporising temperature of the contaminants may be lowered to ambient temperatures when vacuum is applied, initially. At this point the contaminants may vaporise drawing heat from the infiltrating material in the retort, as well as from the instrument's heating system. Additionally, in this circumstance, the rate of vaporising may become uncontrolled.

Furthermore, when infiltrating material becomes contaminated with reagent, in general the volatile reagents may be removed by heating the material under vacuum, hence prolonging the life of the wax. If they have such an available function, many related art tissue processors perform this cleaning of material by transferring the infiltrating material to the instrument's retort and evacuating the material of its contaminants there within the retort. This has a number of shortcomings, identified as follows using the example of paraffin wax as the infiltrating material. Firstly only one wax bath at a time may be cleaned. Second, the instrument may not be used to process tissue while the wax cleaning is in progress. Third, the retort will require cleaning before it may be used again. Fourth, because of the time constraints imposed by the first three identified shortcomings it is usually not possible to allow the wax to be cleaned fully. Typically more than 3 hrs per wax bath is required and approximately an hour for the clean protocol to run. Fifth, related art systems do not quantify how clean the wax has become. In other words they do not track the purity of that fluid. An additional factor here is the inability of these systems to tell when the wax is contaminated and needs cleaning. Sixth, the higher the utilisation rate of the instrument the less time is available for performing the wax clean function but the more the wax actually needs to be cleaned. Seventh, often the wax clean function must be manually initiated and hence often is not done at all.

Any discussion of documents, devices, acts or knowledge in this specification is included to explain the context of the invention. It should not be taken as an admission that any of the material formed part of the prior art base or the common general knowledge in the relevant art on or before the priority date of the invention disclosed herein.

SUMMARY OF INVENTION

An object of the present invention is to alleviate at least one disadvantage associated with the technology identified by the inventor hereinabove, or at least provide a useful alternative.

In one aspect the present invention provides a method of treating a tissue processing fluid, the fluid comprising a first processing fluid and a second contaminating fluid, the method comprising the steps of:

gradually varying the pressure of the fluid from an initial pressure level to a first pressure level such that the fluid remains below a vaporising point of the second contaminating fluid and;

heating the fluid to at least a vaporising temperature of the second contaminating fluid.

According to embodiments of this aspect of the present invention the method may further comprise the step of:

maintaining the pressure of the fluid at the first pressure level for a predetermined time interval corresponding to predefined criteria to allow the second contaminating fluid to vaporise in a controlled manner.

The method accordingly may further comprise the step of:

decreasing the pressure of the fluid from the first pressure level to a second pressure level after the predetermined time interval expires to allow substantially any second contaminating fluid remaining within the fluid to vaporise.

In a preferred embodiment, the predefined criteria may comprise one or more of:

a) the concentration of the second contaminating fluid within the fluid decreases to a level such that the vaporising temperature of the second contaminating fluid increases;

b) the fluid temperature reaches a preselected setpoint temperature for a tissue processing step;

c) a preselected number of cycles of an automated tissue processing apparatus.

In another aspect, the present invention provides a method of treating a tissue processing fluid, the fluid comprising a first processing fluid and a second contaminating fluid, the method comprising the steps of:

removing the second contaminating fluid from the fluid by varying at least one of the pressure and temperature of the fluid to allow the second contaminating fluid to vaporise. Furthermore, according to this aspect of the present invention the method may further comprise the step of:

interleaving the step of removing with one or more tissue processing protocol steps.

In yet another embodiment, the present invention provides apparatus adapted for treating a tissue processing fluid, said apparatus comprising:

processor means adapted to operate in accordance with a predetermined instruction set, said apparatus, in conjunction with said instruction set, being adapted to perform a method of treating a tissue processing fluid as disclosed herein. Preferably the apparatus comprises a histological tissue sample processor.

In another embodiment of the invention there is provided a computer program product comprising:

a computer usable medium having computer readable program code and computer readable system code embodied on said medium for operating in conjunction with a data processing system, said computer program product comprising:

computer readable code within said computer usable medium for performing a method of treating a tissue processing fluid as disclosed herein.

In a further aspect, the present invention provides a method of determining the purity of a tissue processing fluid, the fluid comprising a first processing fluid and a second contaminating fluid, the method comprising the steps of:

determining the volume of second contaminating fluid remaining in the fluid after the pressure of the fluid is varied to a first vacuum level.

Preferably, the method further comprises the steps of:

weighting the determined volume with a first modelling reference corresponding to the first vacuum level;

determining the purity of the fluid in accordance with the weighted volume.

In yet a further embodiment, the present invention provides apparatus adapted for determining the purity of a tissue processing fluid, said apparatus comprising:

processor means adapted to operate in accordance with a predetermined instruction set, said apparatus, in conjunction with said instruction set, being adapted to perform the method of determining the purity of a tissue processing fluid as disclosed herein. Preferably the apparatus comprises a histological tissue sample processor.

In still a further embodiment of the invention there is provided a computer program product comprising:

a computer usable medium having computer readable program code and computer readable system code embodied on said medium for operating in conjunction with a data processing system, said computer program product comprising:

computer readable code within said computer usable medium for performing the method of determining the purity of a tissue processing fluid as disclosed herein.

The present invention provides a number of advantages namely:

Controlled vaporization of contaminants of infiltrating materials, particularly in relation to the operation of Xylene-free tissue processors where the last fluid reagent in the staged processing normally has a relatively low vaporising temperature compared to the processing temperatures of the infiltrating materials such as paraffin wax.

Wax baths may be cleaned simultaneously and advantageously this means that no retort cleaning function is required.

Wax cleaning functions may be performed at all times, even when protocols are running on the retorts of the tissue processing instrument. Thus the instrument may be run at its maximum possible utilisation rate and still have the wax cleaning function operate at close to its maximum efficiency.

Wax cleaning may be turned off when contamination levels reach the required level to prevent excessive pump wear.

Utilisation rates of tissue processing instruments and materials may be greatly increased, for example, having the wax cleaning operating continuously in conjunction with tissue processing protocols may significantly decrease the usage of wax and hence the cost of operation.

Modelling of wax purity may also reduce wax usage and increase pump life by allowing wax cleaning to be switched off when it has achieved its purpose.

Other preferred forms, aspects and embodiments are disclosed in the following detailed description of the invention and the appended claims, forming a part of the description of the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

Further disclosure, improvements, advantages, features and aspects of embodiments of the present invention may be better understood by those skilled in the relevant art by reference to the following description of preferred embodiments taken in conjunction with the accompanying drawings, which are given by way of illustration only, and thus are not limiting to the scope of the present invention, and in which.

DETAILED DESCRIPTION

Figure 1:
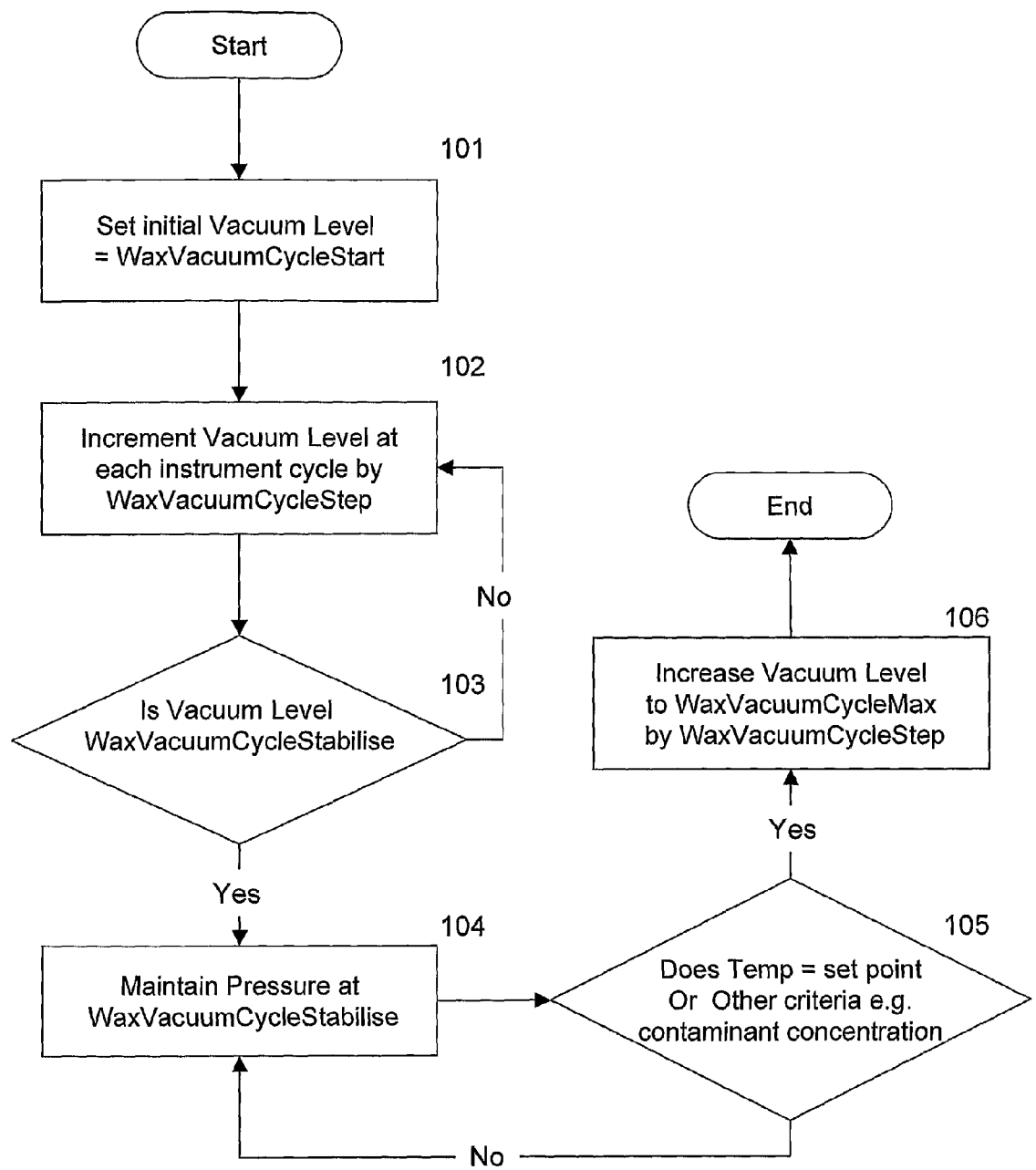
FIG. 1 is a flow chart of a method of treating a tissue processing fluid in accordance with an embodiment of the invention.

A first preferred embodiment of the present invention provides a method of treating a tissue processing fluid, the fluid comprising a first processing fluid and a second contaminating fluid, the method comprising the steps of:

gradually varying the pressure of the fluid from an initial pressure level to a first pressure level such that the fluid remains below a vaporising point of the second contaminating fluid;

heating the fluid to at least a vaporising temperature of the second contaminating fluid.

The method of this first embodiment may further comprise the step of:

controlling the rate at which the second contaminating fluid vaporises by varying the heating of the fluid when the temperature of the fluid reaches at least the vaporising temperature of the second contaminating fluid.

Preferably, the first processing fluid disclosed herein has a vaporising temperature substantially higher than that of the second contaminating fluid. In the first method disclosed above, the first pressure level may be about −40 ka and the second pressure level may be at a level used for tissue processing, for example, of about −80 kPa. The step of varying the pressure of the fluid from an initial pressure level to a first pressure level is preferably characterised by gradually decreasing the pressure by increments of about 10 kPa from an initial pressure level of about −20 kPa.

The first processing fluid disclosed herein is preferably tissue infiltrating material comprising paraffin wax. The second contaminating fluid disclosed herein may comprise a clearing reagent. Alternatively, the second contaminating fluid may comprise a dehydrating reagent. Moreover, the second contaminating fluid may comprise one of:

a) an alcohol;
b) chloroform;
c) xylene;
d) toluene;
e) d-limonene derivatives;
f) acetone/ketones;
g) water or aqueous solutions;
h) proprietary reagents or mixtures such as histoclear™ etc;
i) oils.

Preferably, the tissue processing fluid disclosed herein is treated within a vessel comprising at least one of:
 a) one or more tissue processing retorts;
 b) one or more tissue processing fluid storage baths;
 c) a tissue processing fluid line connecting one or more retorts and storage baths;
 d) an enclosure surrounding fluid storage baths.

In another preferred embodiment of the present invention there is provided a method of treating a tissue processing fluid, the fluid comprising a first processing fluid and a second contaminating fluid, the method comprising the step of:
 removing the second contaminating fluid from the fluid by varying at least one of the pressure and temperature of the fluid so as to allow the second contaminating fluid to vaporise. The preferred method also comprises the step of:
 interleaving the step of removing with one or more tissue processing protocol steps.

Preferably, the step of interleaving comprises:
 a) determining a priority for one or more of the tissue processing protocol and removing steps;
 b) altering the duration of the one or more steps in accordance with their determined priority.

The step of removing may further comprise decreasing the pressure of the fluid to a level below an ambient pressure level.

In a final preferred embodiment, the present invention provides a method of determining the purity of a tissue processing fluid, the fluid comprising a first processing fluid and a second contaminating fluid, the method comprising the step of:
 determining the volume of second contaminating fluid remaining in the fluid after the pressure of the fluid is varied to a first vacuum level. In this preferred embodiment further steps are incorporated, namely:
 weighting the determined volume with a first modelling reference corresponding to the first vacuum level, and;
 determining the purity of the fluid in accordance with the weighted volume.

In this embodiment of determining the purity of a tissue processing fluid the method steps are preferably repeated at a regular time interval. The weighting may comprise a multiplication operation. In a preferred embodiment, the first vacuum level of the above method of determining purity is one of:
 a) about −65 kPa with a corresponding first modelling reference of 0.99, and;
 b) about −20 kPa with a corresponding first modelling reference of 0.997.

Figure 3:
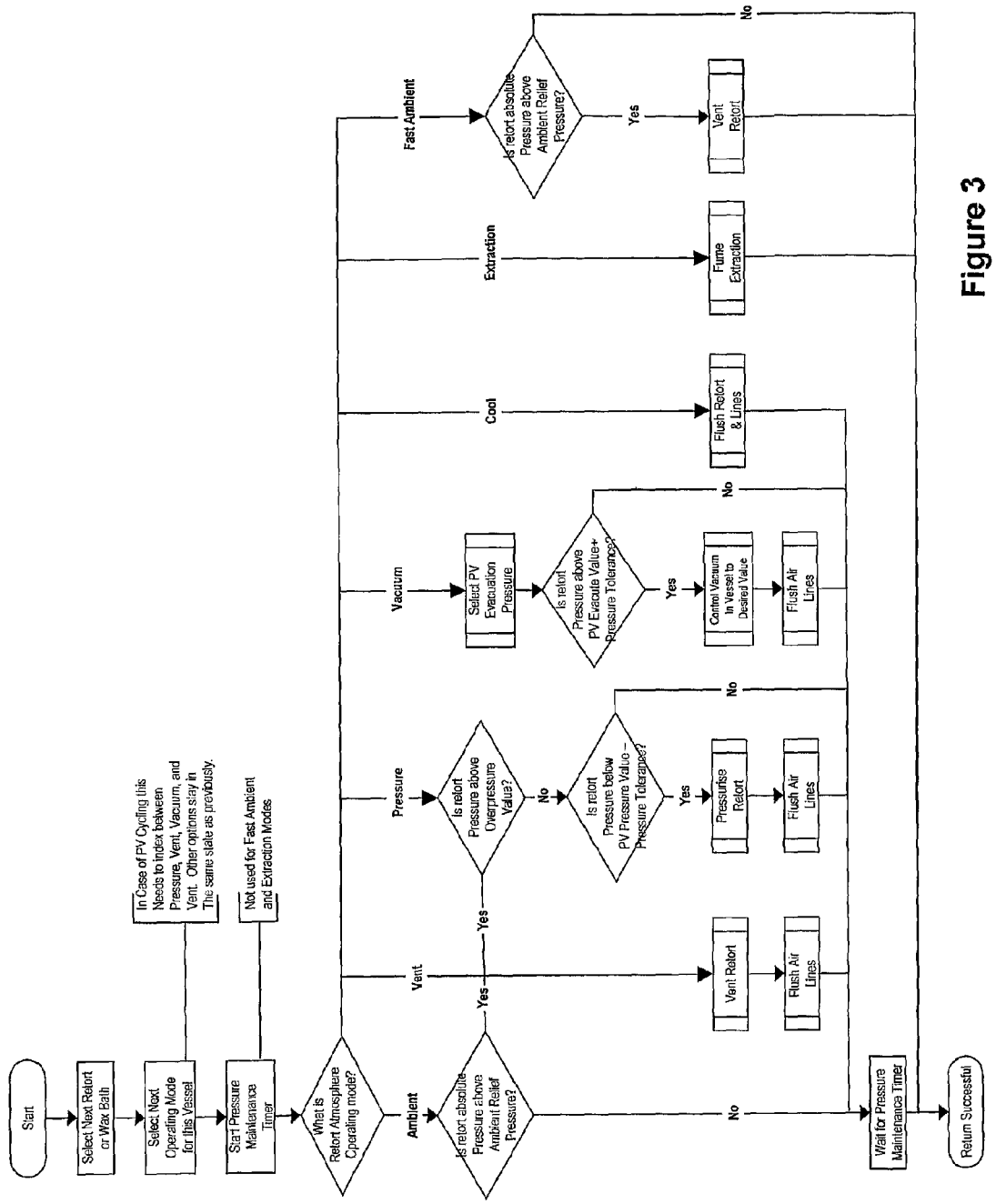
FIG. 3 is a flow chart illustrating the operation of a Pressure Vacuum Cycle for a fluid vessel of a tissue processor in accordance with an embodiment of the present invention.

Applicant's co pending International Application no's. PCT/AU02/01337 (WO 03/029845) and PCT/AU2004/01337 (WO 05/031312) are both incorporated herein by reference. A tissue processor of the type disclosed in the above referenced PCT applications functions in accordance with a number of algorithms or workflows dedicated to different sub-systems within the tissue processor. Examples are the reagent management sub-system and the sub-system that controls the heaters for the retorts. An example workflow relating to the Pressure-Vacuum (PV) Cycle Time Filler is illustrated in FIG. 3 in the form of a flow chart. The purpose of the PV Cycle Time filler is to maintain pressure during the progress of a protocol step and perform any needed background operation. The inputs to the PV Cycle workflow may comprise:
 Set pressure (including whether cycle or ambient)
 Cycle Time
 Evacuation Temperature for Reagent in Vessel In operation, the following is observed. All pressure vacuum cycle filler actions are subject to the availability of the fluidics, which comprises the mechanical systems for storing, holding and transporting fluids and, the corresponding fluids themselves. Pressure Vacuum and Ambient Cycles are called directly from the protocol. If a PV Cycle is requested in a given protocol then the system may alternate between cycles in the following order Pressure, Vent, Vacuum, Vent, and then repeated. Vent and Cool Cycles, Fast Ambient, and Extraction may not be called directly from a protocol. Vacuum and Cool Cycles may be called from a dry action step. Fast Ambient & Extraction Cycles may be called during a fume extraction state while accessing the retort. Evacuate chamber may be done for the retort under consideration and set for timed evacuation rather than to the set pressure. Preferably, the following configuration values are used as shown in Table 1.

TABLE 1

| Identifier | Default value | Meaning |
| --- | --- | --- |
| FreshAirFlushShort | 5 sec | Used as a subroutine parameter for Flush Air Lines below in Table 2 |
| MaxWaxTemp | 100° C. | Maximum temperature above which wax bath should not accept evacuation |
| OverpressureValue | 49.5 kPa | Pressure at which automatic pressure relief is required |
| AmbientReliefPressure | 30 kPa | Pressure at which vent will occur if running at ambient pressure |
| PressureTolerance | 2.5 kPa | Pressure above and below the set pressure tolerated |
| PressureUpdateTime | 30 sec | The time between successive Pressure/Vacuum cycles |
| PVPressureValue | 40 kPa | Operating Pressure |
| Reagent Vaporising Point | 100° C. | Based on the reagent in the retort (or 100° C. if required pressure is ambient accounting for wax clean) to allow the evacuate routine to determine whether the reagent can be evacuated. |
| PVRetortEvacuateTime/ PVRetortPressureTime | PressureUpdate Time- FreshAirFlushShort | Maximum time available to attempt to reach retort evacuation pressure |

The following parameters may be used during the PV Cycle Filler. All specified parameters may be stored as configuration values.

TABLE 2

| Sub-routine | Parameter | Value | Meaning |
| --- | --- | --- | --- |
| Flush Air Lines | Fresh air | 5 sec | Time to spend flushing with fresh air. This is based on FreshAirFlushShort above. |
| Evacuate Chamber | PVRetortEvacuateTime | 25 sec | Time to wait for a retort to reach the specified vacuum before a timeout when evacuating a retort. |

TABLE 2-continued

| Sub-routine | Parameter | Value | Meaning |
|---|---|---|---|
| | PVEvacuateValue | See Discussion Below & Table 3 | This is based on RetortEvacuation Time above in Table 1 Target Vacuum to achieve |
| Pressurise Retort | PVRetortPressureTime | 25 sec | Time to wait for a retort to reach the specified pressure before a timeout when pressurising a retort. This is based on RetortPressurisationTime above |
| | PVPressureValue | 40 kPa | Target Pressure to achieve |
| Flush Retort & Lines | Fresh Air | 30 sec | Time to spend flushing with fresh air, based on PressureUpdateTime in Table 1 above |

Further explanation of the operation of other sub-systems of a tissue processor, in particular, the Xylene-free tissue processor sold under the name Peloris™ by Vision BioSystems™ Limited may be gained from the specifications of the above-referenced related PCT patent application no's. PCT/AU02/01337 (WO 03/029845) and PCT/AU2004/01337 (WO 05/031312).

In accordance with a preferred embodiment of the invention the pressure or vacuum conditions applied to tissue processing fluids, for the purpose of evacuating a fluid of its contaminants, are selected and controlled by the PV Cycle Filler Time workflow illustrated in FIG. 3 and, more particularly with reference to FIG. 1. A purpose of this routine is to set the current evacuation requirements for a retort or wax bath or, other vessel within the processor for containing fluid, to use during PV cycling. The following configuration values maybe used as typical values as shown below in table 3.

TABLE 3

| Identifier | Default value | Meaning |
|---|---|---|
| DefaultPVEvacuateValue | −80 kPa | Default Vacuum to evacuate to |
| WaxVacuumCycleMax_kpa | −80 kPa | Final Vacuum level to achieve in wax steps |
| WaxVacuumCycleStart_kpa | −20 kPa | Initial vacuum used on first wax step of a protocol |
| WaxVacuumCycleStep_kpa | −10 kPa | Increase in vacuum used for each successive PV cycle |
| WaxVacuumCycleStabilise_kpa | −40 kPa | Vacuum level to stabilise at until retort is at set operating temp or specified criteria |
| WaxVacuumCycleStepsAtStabiliseVacuum | 3 | Minimum number of cycles to remain at the stabilisation vacuum level |

Figure 2:
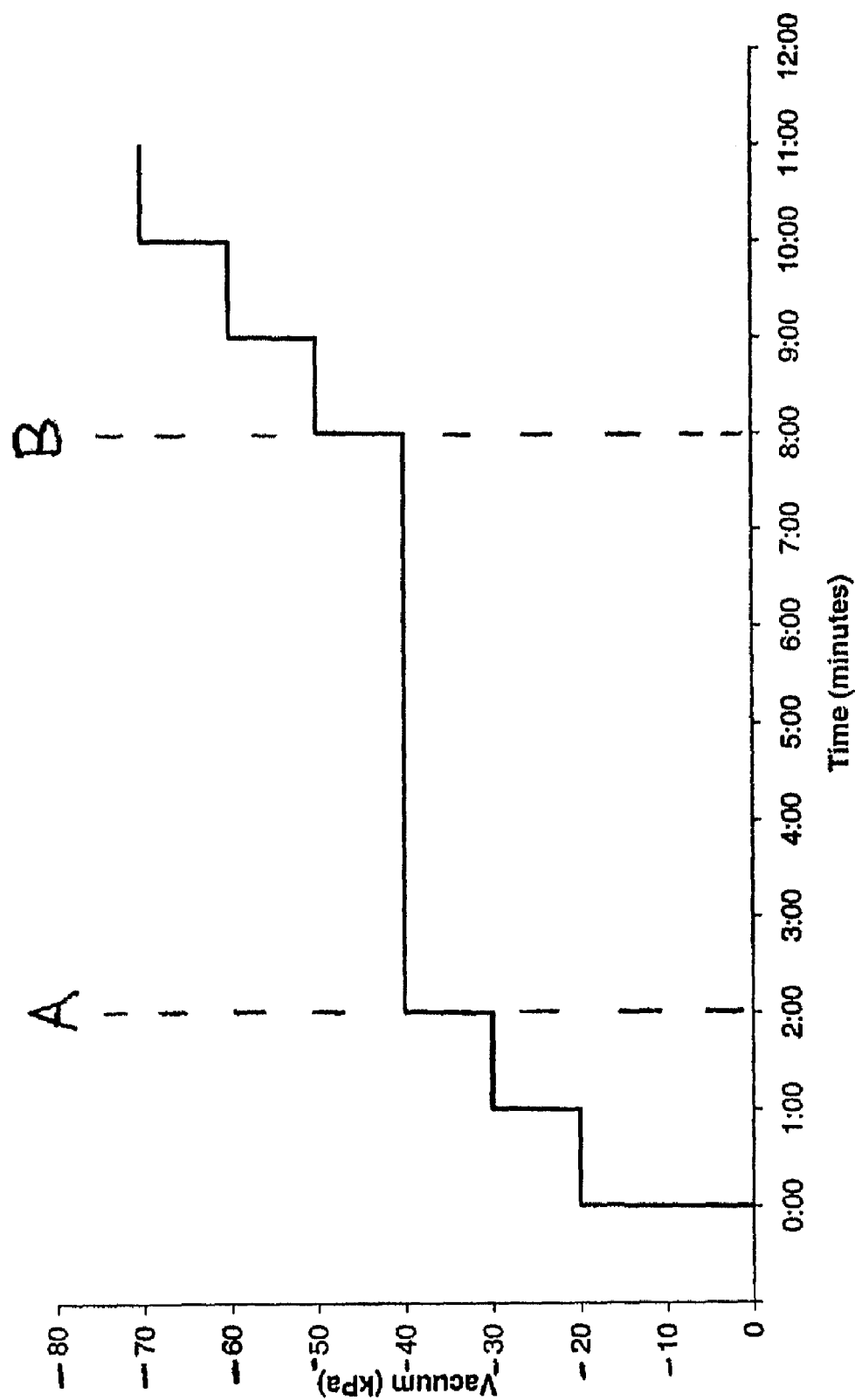
FIG. 2 is a time interval diagram illustrating the pressure relationship of a tissue processing fluid over time in accordance with the embodiment of FIG. 1.

In the case of the vessel being the retort, the current reagent in the retort being wax and the previous reagent not being wax, then initially the target vacuum level is set to WaxVacuumCycleStart. This is shown as the −20 kPa level in FIG. 2. For each successive evacuation cycle that is completed on this retort the vacuum level is increased by WaxVacuumCycleStep until the vacuum level is at the WaxVacuumCycleStabilise level. This is illustrated by the stepwise behaviour in FIG. 2 up to a vacuum pressure level of about −40 kPa and shown at point A of FIG. 2. The vacuum then remains at this level for at least WaxVacuumStepsAtStabiliseVacuum cycles or until the retort is at its setpoint temperature. This is illustrated in FIG. 2 by the plateau in the graph at −40 kPa between point A and point B of FIG. 2. At this stage the vacuum level may be increased by WaxVacuumCycleStep per cycle until the level reaches WaxVacuumCycleMax. In all other instances the vacuum level may be set at the DefaultPVEvacuateValue.

With reference to the flow chart of FIG. 1, a preferred embodiment is described. At step 101, an initial vacuum level of WaxVacuumCycleStart is obtained similar to that illustrated by FIG. 2 showing −20 kPa. Whereas related art systems apply the maximum operational vacuum levels immediately, instead in the preferred embodiment, step 102 of FIG. 1, the vacuum is gradually increased (pressure is decreased) to a constant low level of WaxVacuum CycleStabilise, see step 103 of FIG. 1 and point A of FIG. 2. The gradual increase in vacuum, step 102 of FIG. 1, is preferably performed by increments of WaxVacuumCycleStep at each cycle of the tissue processor. At step 104 of FIG. 1, the relatively low vacuum level is maintained. This relatively constant low level of vacuum is intended not to boil the wax at its initial temperature. Heating may be applied throughout the process and further heating may also be applied at step 105 of FIG. 1, which raises the temperature of the wax. When the wax reaches the vaporising temperature of the contaminant in the mix the contaminant will start to boil off. An example contaminant is isopropanol. At this point in time the rate of temperature increase of the wax will drop to essentially zero and all the energy supplied by the heating system will be used in evaporating the contaminant. Thus by controlling or limiting the heater power it is possible to limit the vaporising rate of the contaminant. As the contaminant boils off the concentration of the contaminant in the wax will drop, and the temperature required to vaporise the contaminant will increase. This means that the temperature of the wax mixture will slowly rise as the contaminant boils off. Once the mixture reaches its final temperature or, alternately the concentration of the contaminant reaches a sufficiently low level, (see point B of FIG. 2) it is then safe to increase the vacuum level to draw off any remaining contaminant in the wax (shown at step 106 of FIG. 1). At the end of the process the level of contaminant in the wax has been reduced to the minimum level achievable with the defined conditions of temperature and pressure but the vaporising rate has been controlled to limit foam production. In another more preferred embodiment, a similar method of treatment is applied to a tissue processing fluid, namely, infiltrating material such as paraffin wax. In this preferred embodiment the configuration values of Table 3 may be altered as follows in Table 4:

TABLE 4

| Identifier | Default value | Meaning |
|---|---|---|
| DefaultPVEvacuateValue | −80 kPa | Default Vacuum to evacuate to |
| WaxVacuumCycleMax_kpa | −80 kPa | Final Vacuum level to achieve in wax steps |
| WaxVacuumCycleStart_kpa | −40 kPa | Initial vacuum used on first wax step of a protocol |

TABLE 4-continued

| Identifier | Default value | Meaning |
|---|---|---|
| WaxVacuumCycleStep_kpa | −5 kPa | Increase in vacuum used for each successive PV cycle |
| WaxVacuumCycleStabilise_kpa | −40 kPa | Vacuum level to stabilise at until retort is at set operating temp or specified criteria |
| WaxVacuumCycleStepsAtStabiliseVacuum | 8 | Minimum number of cycles to remain at the stabilisation vacuum level |

Accordingly, taking the configuration values of Table 3 and Table 4 into account, the conditions under which the PV Cycle Filler Time workflow operates in accordance with the present invention may comprise the following:
- initial vacuum (or pressure level) used may be in the range of −10 kPa to −50 kPa and preferably −20 kPa to −40 kPa. In a particularly preferred embodiment, the initial vacuum may be −40 kPa;
- incremental increase in vacuum used may be in the range of −15 kPa to −1 kPa and preferably −10 kPa to −5 kPa. In a particularly preferred embodiment, the incremental increase is −5 kPa. Of course this corresponds to an absolute increment in pressure of 5 kPa;
- the minimum number of cycles in which the vacuum level remains stabilised may be in the range of 2 to 10 cycles and preferably 3 to 8 cycles.

In a particularly preferred embodiment, the number of cycles may be 8.

The embodiments described above are particularly useful in relation to the operation of Xylene-free tissue processors where the last fluid reagent in the staged processing normally has a relatively low vaporising temperature compared to the processing temperatures of the infiltrating materials such as paraffin wax. As an example, isopropanol has a much lower vaporising temperature than paraffin wax. It is also possible that clearing agents, for example chloroform or Xylene, may also conform to this scenario as they may have relatively low vaporising points compared to paraffin wax.

In another embodiment, it is proposed to make the wax baths containing infiltrating material pressure tight and perform wax cleaning in the wax baths. This allows all wax baths to be cleaned simultaneously and advantageously means that no retort cleaning function is required. It may also be performed in all idle times of the tissue processing instrument. A further embodiment involves using a time sharing arrangement to allow the wax cleaning function to be performed at all times, even when protocols are running on the retorts of the instrument. This essentially means that a wax cleaning function may run continually. This allows the instrument to be run at its maximum possible utilisation rate and still have the wax cleaning function operate at close to its maximum efficiency. In yet another embodiment, wax cleaning may be performed by utilising the reagent management and tracking system disclosed in Applicant's co pending International (PCT) Application No PCT/AU2004/01337 (WO 05/031312), incorporated herein by reference, which tracks actual concentrations of reagents by modelling reagent carryover volumes. The reagent management functions may be enhanced in a further embodiment by modelling how the volatile reagent fractions within a fluid are removed by the wax cleaning function. This may be modelled by weighting the volume of the volatile fraction by a numerical modelling reference, for example 0.99, every time the wax bath is successfully evacuated to a given vacuum level, say of −65 kPa. The weighting, which may be in the form of a multiplication, may be performed at regular time intervals. Preferably, the regular time interval is approximately once every minute. If a lower vacuum level is reached then a correspondingly different weighting may be performed. For example, a different multiplier such as 0.997 at −20 kPa may be used. Alternatively, no weighting at all (or equivalently, a weighting factor of 1) may be used in cases were the evacuation of the wax fails for some reason, for example, an operator leaves a lid or cover open in the Tissue Processor. The modelled weighting may account for degradation of the wax bath sealing systems or, for manual intervention by opening the wax bath lids etc. Non-volatile fractions may be cleaned at much lower rates, in accordance with the weighted modelling or, not at all. Therefore, the preferred system still accounts for such systems. Wax cleaning may be turned off when contamination levels reach the required level in order to prevent excessive pump wear.

Specific examples of preferred embodiments of the modelling are illustrated by the following parameters for contaminants such as dehydrants and clearants. The examples given are based on an infiltrating material temperature of 65° C. The example dehydrant is isopropanol and the example clearant is Xylene:

---
[WaxCleaningVacuumLevel 1]

Vacuum (kPA) = 0
DehydrantMultiplier = 1.0
ClearantMultiplier = 1.0
[WaxCleaningVacuumLevel 2]

Vacuum (kPA) = −20
DehydrantMultiplier = 0.997
ClearantMultiplier = 0.9995
[WaxCleaningVacuumLevel 3]

Vacuum (kPA) = −40
DehydrantMultiplier = 0.994
ClearantMultiplier = 0.999
[WaxCleaningVacuumLevel 4]

Vacuum (kPA) = −60
DehydrantMultiplier = 0.99
ClearantMultiplier = 0.997
---

It is also envisaged that longer evacuation times may be utilised within tissue processors as described herein. Current usage in the tissue processors referenced herein is to evacuate for 30 secs every 90 secs. It is envisaged that the present invention may be applied to evacuation of 60 secs every 180 secs. The parameters discussed here may be adjusted for accuracy given differing laboratory situations, for example, if an original estimate of purity overestimates the amount of isopropanol removed. In this case, the following approximate parameter ranges may be used. Again, the examples given are based on an infiltrating material temperature of 65° C., the example dehydrant is isopropanol and the example clearant is Xylene:

---
[WaxCleaningVacuumLevel 1]

Vacuum (kPA) = 0
DehydrantMultiplier = 1.0
ClearantMultiplier = 1.0

-continued

[WaxCleaningVacuumLevel 2]

Vacuum (kPA) = −20
DehydrantMultiplier = 0.996 to 0.998
ClearantMultiplier = 0.9994 to 9997
[WaxCleaningVacuumLevel 3]

Vacuum (kPA) = −40
DehydrantMultiplier = 0.992 to 0.996
ClearantMultiplier = 0.9986 to 9993
[WaxCleaningVacuumLevel 4]

Vacuum (kPA) = −60
DehydrantMultiplier = 0.986 to 0.993
ClearantMultiplier = 0.996 to 0.998

Advantageously, effective utilisation rates of tissue processing instruments may be greatly increased in accordance with the above embodiments. For example, having the wax cleaning operating continuously in conjunction with tissue processing protocols may significantly decrease the usage of wax and hence the cost of operation. Modelling of wax purity may also reduce wax usage and increase pump life by allowing wax cleaning to be switched off when it has achieved its purpose.

While this invention has been described in connection with specific embodiments thereof, it will be understood that it is capable of further modification(s). This application is intended to cover any variations uses or adaptations of the invention following in general, the principles of the invention and comprising such departures from the present disclosure as come within known or customary practice within the art to which the invention pertains and as may be applied to the essential features hereinbefore set forth.

As the present invention may be embodied in several forms without departing from the spirit of the essential characteristics of the invention, it should be understood that the above described embodiments are not to limit the present invention unless otherwise specified, but rather should be construed broadly within the spirit and scope of the invention defined in the appended claims. Various modifications and equivalent arrangements are intended to be included within the spirit and scope of the invention and the appended claims. Therefore, the specific embodiments are to be understood to be illustrative of the many ways in which the principles of the present invention may be practiced. In the following claims, means-plus-function clauses are intended to cover structures as performing the defined function and not only structural equivalents, but also equivalent structures. For example, although a nail and a screw may not be structural equivalents in that a nail employs a cylindrical surface to secure wooden parts together, whereas a screw employs a helical surface to secure wooden parts together, in the environment of fastening wooden parts, a nail and a screw are equivalent structures.

"Comprises/comprising" when used in this specification is taken to specify the presence of stated features, integers, steps or components but does not preclude the presence or addition of one or more other features, integers, steps, components or groups thereof."

The invention claimed is:

1. A method of treating a tissue processing fluid, the fluid comprising a first processing fluid and a second contaminating fluid, the method comprising the steps of:
   gradually varying the pressure of the fluid from an initial pressure level to a first pressure level above a vapor pressure of the second contaminating fluid such that a temperature of the fluid is below a vaporizing temperature of the second contaminating fluid at the first pressure of the fluid;
   then maintaining the pressure of the fluid at the first pressure level while applying heat to the fluid to heat the fluid to at least the vaporizing temperature of the second contaminating fluid.

2. A method as claimed in claim 1 further comprising the step of:
   maintaining the pressure of the fluid at the first pressure level for a predetermined time interval in which said time interval corresponds to predefined criteria so as to allow the second contaminating fluid to vaporise in a controlled manner.

3. A method as claimed in claim 2 further comprising the step of;
   decreasing the pressure of the fluid from the first pressure level to a second pressure level after the predetermined time interval expires to allow substantially any second contaminating fluid remaining within the fluid to vaporise.

4. A method as claimed in claim 3 wherein the predefined criteria comprises one or more of:
   a) the concentration of the second contaminating fluid within the fluid decreases to a level such that the vaporising temperature of the second contaminating fluid increases;
   b) the fluid temperature reaches a preselected setpoint temperature for a tissue processing step;
   c) a preselected number of cycles of an automated tissue processing apparatus is completed.

5. A method as claimed in claim 4 wherein the gradual variation of pressure from the initial pressure level to the first pressure level comprises an incremental variation.

6. A method as claimed in claim 5 wherein the incremental variation in pressure comprises increments in the range of about 1kPa to 15kPa.

7. A method as claimed in claim 5 wherein the initial pressure level is in the range of about −10 kPa to −50 kPa.

8. A method as claimed in claim 5 further comprising the step of:
   controlling the rate at which the second contaminating fluid vaporizes by varying the heating of the fluid when the temperature of the fluid reaches at least the vaporizing temperature of the second contaminating fluid.

9. A method as claimed in claim 1 wherein the vaporizing temperature of the first processing fluid is substantially higher than that of the second contaminating fluid.

10. A method as claimed in claim 1 wherein the first pressure level is about −40 kPa.

11. A method as claimed in claim 3 wherein the second pressure level is a tissue processing pressure level of about −80 kPa.

12. A method as claimed in claim 1 wherein the first processing fluid comprises tissue infiltrating material.

13. A method as claimed in claim 12 wherein the tissue infiltrating material comprises paraffin wax.

14. A method as claimed in claim 1 wherein the second contaminating fluid comprises at least one of:
   a clearing reagent, and;
   a dehydrating reagent.

15. A method as claimed in claim 14 wherein the second contaminating fluid comprises one or more of:
   a) an alcohol;
   b) chloroform;
   c) xylene;
   d) toluene;

e) d-limonene derivatives;
f) acetone/ketones;
g) water or aqueous solutions;
h) proprietary reagents or mixtures such as histoclear™ etc;
i) oils.

16. A method as claimed in claim 1 wherein the tissue processing fluid is treated within a vessel comprising at least one of:
   a) one or more tissue processing retorts;
   b) one or more tissue processing fluid storage baths;
   c) a tissue processing fluid line connecting one or more retorts and storage baths;
   d) an enclosure surrounding fluid storage baths.

17. A method as claimed in claim 1 wherein the method steps are performed during one or more sub-procedures of a tissue processing protocol.

18. A method of treating a tissue processing fluid, the fluid comprising a first processing fluid and a second contaminating fluid, the method comprising the step of:
   removing the second contaminating fluid from the fluid by first gradually varying a pressure of the fluid from an initial pressure level to a first pressure level above a vapor pressure of the second contaminating fluid at an initial fluid temperature, while holding the temperature of the fluid at the initial fluid temperature; and
   then gradually varying the temperature of the fluid from the initial fluid temperature to a first temperature level above a vaporizing temperature of the second contaminating fluid at the first pressure level while maintaining the pressure of the fluid at the first pressure level so as to allow the second contaminating fluid to vaporize.

19. A method as claimed in claim 18 further comprising the step of:
   interleaving the step of removing with one or more tissue processing protocol steps.

20. A method as claimed in claim 19 wherein the step of interleaving comprises:
   a) determining a priority for one or more of the tissue processing protocol steps and the removing steps;
   b) altering the duration of the one or more steps in accordance with their determined priority.

21. A method as claimed in 20 wherein the step of removing further comprises:
   decreasing the pressure of the fluid to a level below an ambient pressure level.

* * * * *

UNITED STATES PATENT AND TRADEMARK OFFICE
CERTIFICATE OF CORRECTION

PATENT NO. : 8,409,871 B2
APPLICATION NO. : 11/569658
DATED : April 2, 2013
INVENTOR(S) : Michael Houston Drummond It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1773 days.

Signed and Sealed this
First Day of September, 2015

Michelle K. Lee
*Director of the United States Patent and Trademark Office*